United States Patent [19]

Yamakawa

[11] Patent Number: 5,006,660

[45] Date of Patent: Apr. 9, 1991

[54] PROCESS FOR PRODUCING ALKOXYBENZENE COMPOUND AND ARYLOXYBENZENE COMPOUND

[75] Inventor: Katsuyoshi Yamakawa, Minami-ashigara, Japan

[73] Assignee: Fuji Photo Film Co., Ltd., Kanagawa, Japan

[21] Appl. No.: 372,544

[22] Filed: Jun. 28, 1989

[30] Foreign Application Priority Data

Jun. 29, 1988 [JP] Japan ................................ 63-159419

[51] Int. Cl.$^5$ .................. C07C 231/12; C07D 213/74
[52] U.S. Cl. .................................... 546/316; 534/681;
544/297; 548/197; 548/217; 548/259; 548/306;
548/363; 549/362; 549/437; 558/417; 558/418;
558/426; 560/29; 560/45; 562/58; 562/452;
562/453; 564/50; 564/86; 564/99; 564/151;
564/158; 564/176; 564/184; 564/223; 564/430;
564/443
[58] Field of Search .................. 534/681; 544/297;
546/316; 548/197, 217, 259, 306, 363; 549/362,
437; 558/417, 418, 426; 560/29, 45; 562/58,
173, 452, 453; 564/50, 86, 99, 151, 158, 176,
184, 223, 430, 443

[56] References Cited

U.S. PATENT DOCUMENTS 4,060,612 11/1977 Kikumoto et al. ............. 564/353 X
4,603,222 7/1986 Tang et al. ..................... 564/430 X
4,754,068 6/1988 Yamaguchi et al. ................ 564/430

OTHER PUBLICATIONS

Wagner et al., "Synthetic Organic Chemistry", pp. 226-227 (1963).
Advanced Organic Chemistry, Reactions, Mechanisms, and Structure, Third Edition, Jerry March, p. 584, McGraw Hill, (1977).

Primary Examiner—Richard L. Raymond
Attorney, Agent, or Firm—Birch, Stewart, Kolasch & Birch

[57] ABSTRACT

The present invention relates to a process for producing an alkoxybenzene compound or an aryloxybenzene compound by reacting a halogenobenzene compound with an alcohol or a phenol compound in the presence of copper or a copper compound, an amine, and a base. According to the disclosure, an alkoxybenzene compound and an aryloxybenzene compound can be produced under moderate conditions in good yield with high selectivity.

23 Claims, No Drawings

PROCESS FOR PRODUCING ALKOXYBENZENE COMPOUND AND ARYLOXYBENZENE COMPOUND

FIELD OF THE INVENTION

The present invention relates to a process for producing an alkoxybenzene compound and an aryloxybenzene compound.

BACKGROUND OF THE INVENTION

An alkoxybenzene compound and an aryloxybenzene compound are very useful industrially, and, for example, 4-alkoxy-2,5-diacylphenols and 4-aryloxy-2,5-diacylaminophenols recently are attracting attention as a cyan coupler in the field of photographic chemistry [see JP-A ("JP-A" means unexamined published Japanese patent application) Nos. 35731/1985 and 49336/1985 and U.S. Pat. No. 4,579,813].

The alkoxybenzene compound and aryloxybenzene compound having a substituted amino group at the ortho position are quite important intermediates for the synthesis of many industrially useful compounds, such as photographic color mixing inhibitors (e.g., JP-A No. 81341/1988), chelate dyes (*J. Org. Chem.*, 47, 2607 (1982)), and antibacterial agents (*J. Med. Chem.*, 28 24 (1985)).

Also, a variety of applications of the alkoxybenzene compound and the aryloxybenzene compound includes use as a synthesis intermediate from which dyes and physiologically active compounds (e.g., pharmaceuticals and agricultural chemicals) can be derived.

A typical conventional process of synthetically producing these alkoxybenzene compounds and aryloxybenzene compounds is the one represented by the following scheme 1.

That is, generally, the alkoxybenzene compound or the aryloxybenzene compounds represented by formula (X) are produced by using, as a starting raw material, a phenol compound (III), introducing a nitrogen atom to the ortho position of the phenol by nitration or diazocoupling, and then carrying out alkylation or amidenation.

In the process of the scheme 1, aniline compound represented by formula (VI) or (VIII) is readily oxidized and colored intensively and thus low in purity in many cases. Under nitration conditions in the process from (III) to (IV), quinone is produced, in many cases, by the oxidation reaction (for example, when a halogen atom or alkoxyl group is present on the benzene ring: see *J. Chem. Soc.*, 1963, 3028; *J. Am. Chem. Soc.*, 71, 3953 (1949); and *J. Org. Chem.*, 4, 555 (1939)). Further, in the synthesis of (VII) from (III) by diazo-coupling, the productivity is low in many cases, since a large amount of solvent is required.

Further, it is quite difficult to convert from (III) to (IV) and from (III) to (VII) selectively with respect to the position.

SUMMARY OF THE INVENTION

Therefore, one object of the present invention is to provide a process for synthesizing an alkoxybenzene compound and an aryloxybenzene compound in a good yield under moderate conditions.

The above and other objects, features, and advantages of the invention will become apparent in the following description.

DETAILED DESCRIPTION OF THE INVENTION

The inventor has studied intensively in order to develop a method of introducing an alkoxy group or an

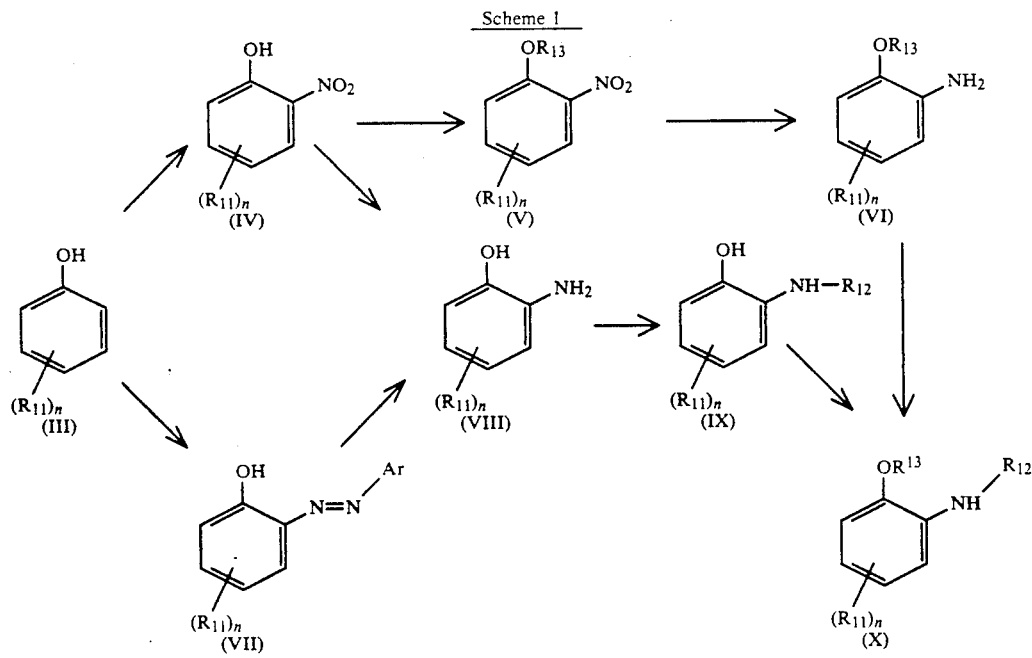

In the above scheme, $R_{11}$ represents a group that is capable of being substituted onto a benzene ring, $R_{12}$ represents an acyl group or the like, $R_{13}$ represents an alkyl group or an aryl group, and n is an integer of 0 to 4.

aryloxy group after the formation of an amido bond, for example, by a method shown in scheme 2 below.

Scheme 2

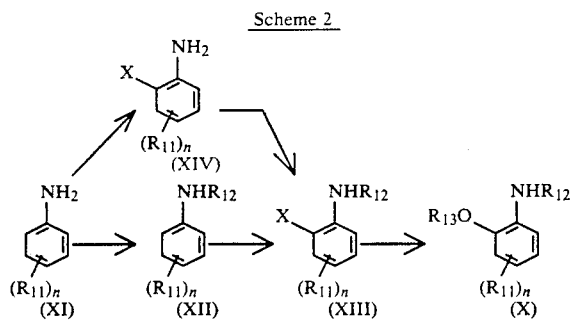

In scheme 2, $R_{11}$, $R_{12}$, $R_{13}$, and n are those as defined above, and X represents a halogen atom.

The inventor also has noted the fact that in the above scheme 2, startling progress in techniques of halogenating aromatic compounds has recently be made, making possible the selective synthesis of (XIV) from (XI) or of (XIII) from (XII) by allowing a halogenating agent to be carried, for example, on alumina or the like. As a result, the inventor has found that when a halogenobenzene compound (XIII) and an alcohol or a phenol compound are reacted in the presence of copper or a copper salt, an amine, and a base, a desired alkoxybenzene compound (X) or aryloxybenzene compound can be obtained under moderate conditions in good yield with high selectivity, completing the above scheme 2.

That is, the present invention provides a process for producing an alkoxybenzene compound and an aryloxybenzene compound, comprising reacting a halogenobenzene compound and an alcohol or phenol compound in the presence of copper or a copper compound, an amine, and a base.

The reaction in the present invention can be represented by the following formula:

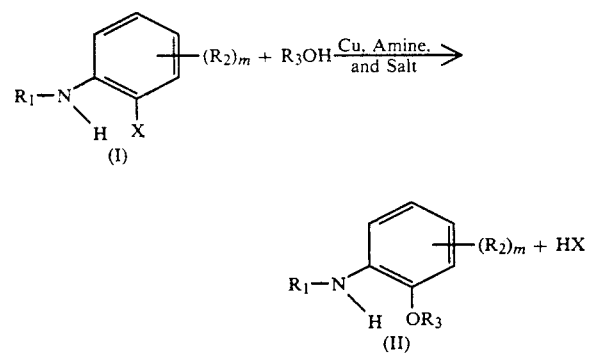

In formula (I), X represents a halogen atom, $R_1$ represents a heterocyclic residue, an acyl group, an alkylsulfonyl group, an arylsulfonyl group, a carbamoyl group, a sulfamoyl group, an alkoxycarbonyl group, an aryloxycarbonyl group, an alkoxysulfonyl group, or an aryloxysulfonyl group, $R_2$ represents a group that is capable of being substituted onto an aromatic ring, m is an integer of 0 to 4, $R_1$ and $R_2$ may bond together to form a 5- to 7-membered ring, $R_2$ groups may bond each other to form a 5- to 7-membered ring, and when m is 2 or over, $R_2$ groups may be the same or different.

In formula (II), $R_3$ represents an alkyl group or an aryl group. In formula (I), X represents a chlorine atom, a bromine atom, an iodine atom, or a fluorine atom, with an iodine atom or a bromine atom preferred.

In formula (I), preferably $R_1$ represents a heterocyclic residue (e.g., pyridine-3-yl), an acyl group having 1 to 36 carbon atoms {e.g., formyl, acetyl, propionyl, pivaloyl, benzoyl, dodecanoyl, 2-ethylhexanoyl, 2-(2,4-di-t-benzylphenoxy)butanoyl, trifluoroacetyl, trichloroacetyl, p-nitrobenzoyl, p-chlorobenzoyl, and pentafluorobenzoyl}, an alkylsulfonyl group having 1 to 36 carbon atoms (e.g., methanesulfonyl, ethanesulfonyl, n-butanesulfonyl, benzylsulfonyl, trifluoromethanesulfonyl, n-dodecanesulfonyl, and n-hexadecanesulfonyl), an arylsulfonyl having 6 to 36 carbon atoms (e.g., phenylsulfonyl, p-tolylsulfonyl, m-nitrophenylsulfonyl, and p-dodecylphenylsulfonyl), or an alkoxycarbonyl group having 2 to 36 carbon atoms (e.g., methoxycarbonyl, ethoxycarbonyl, i-butoxycarbonyl, benzyloxycarbonyl, t-butoxycarbonyl, and dodecyloxycarbonyl).

In formula (I), preferably $R_2$ represents a halogen atom (e.g., fluorine, chlorine, and bromine), an alkyl group having 1 to 18 carbon atoms (e.g., methyl, ethyl, i-propyl, t-butyl, trifluoromethyl, benzyl, and n-dodecyl), a carboxyl group, a sulfo group, a hydroxyl group, a cyano group, a carbamoyl group having 1 to 37 carbon atoms {e.g., carbamoyl, N,N-dimethylcarbamoyl, N,N-diethylcarbamoyl, N-methylcarbamoyl, N-butylcarbamoyl, N-cyclohexylcarbamoyl, N,N-dihexylcarbamoyl, N-dodecylcarbamoyl, N-(3-dodecyloxypropyl)carbamoyl, N-[3-(2,4-di-t-pentylphenoxy)propyl] carbamoyl, and N-[4-(2,4-di-t-pentylphenoxy)butyl]carbamoyl}, a sulfamoyl having 0 to 36 carbon atoms (e.g., sulfamoyl, N-methylsulfamoyl, N-butylsulfamoyl, N,N-dimethylsulfamoyl, N,N-diethylsulfamoyl, and N-dodecylsulfamoyl), a carbonamido group having 1 to 36 carbon atoms (e.g., formamido, acetamido, trifluoroacetamido, propanamido, benzamido, p-nitrobenzamido, and dodecanamido), a sulfonamido group having 1 to 36 carbon atoms (e.g., methanesulfonamido, ethanesulfonamido, butanesulfonamido, trifuloromethanesulfonamido, benzenesulfonamido, p-toluenesulfonamido, benzylsulfonamido, and n-hexadecanesulfonamido), an alkoxy group having 1 to 36 carbon atoms (e.g., methoxy, ethoxy, methoxyethoxy, benzyloxy, and n-dodecyloxy), an alkoxycarbonyl group having 2 to 36 carbon atoms (e.g., methoxycarbonyl, ethoxycarbonyl, and n-dodecyloxycarbonyl), an amino group (e.g., amino, methylamino, dimethylamino, and morpholino), a nitro group, or an acyl group having 1 to 24 carbon atoms (e.g., formyl, acetyl, benzoyl, and dodecanoyl). Of these exemplified substituents, a substituent other than a hydroxyl group of an amino group is more preferable.

In formula (II), preferably $R_3$ represents a primary alkyl group having 1 to 36 carbon atoms {e.g., methyl, ethyl, propyl, benzyl, 2-hydroxyethyl, 3-hydroxypropyl, 2-methoxyethyl, 2-ethylhexyl, allyl, propargyl, phenethyl, 2-phenoxyethyl, 2-(p-nitrophenoxy)ethyl, 2-chloroethyl, 2-bromoethyl, n-hexyl, 2-(2-hydroxyethoxy)ethyl, and p-nitrobenzyl} or a aryl group having 6 to 36 carbon atoms (e.g., phenyl and naphthyl), in which various substituents as described for $R_2$ may be included. More preferably, the substituent on aryl group is selected so as to make the sum of the $\sigma_p$ values 0.0 or lower. As the $\sigma_p$ value, it is preferable to use the value as described by, for example, C. Hansch (*J. Med. Chem.*, 16, 1207(1973); ibid., 20, 304(1977)).

m is preferably 0.

The reaction of the present invention is effected in the presence of copper or a copper compound, an amine, and a base. The copper compound may be any one having an oxidation number of 1 to 2. As the copper compound, preferably a copper salt is used.

As the copper or the copper salt used in the present invention, any known one may be used. Typical examples are the following:

(a) Copper

Copper in the form of a powder, granules, a plate, a chain, or a line.

(b) Copper (I) compounds (anhydride or hydrate)

Cuprous chloride, cuprous bromide, cuprous cyanide, cuprous iodide, cuprous oxide, cuprous thiocyanate, etc.

(c) Copper (II) compounds (anhydride or hydrate)

Copper acetate, copper acetylacetonate, cupric bromide, cupric chloride, cupric citrate, copper diammonium chloride, copper 4-cyclohexylbutyrate, copper formate, copper gluconate, cupric hydroxide, copper nitrate, copper oleate, cupric oxide, cupric phosphate, potassium cupric chloride, copper sulfate, copper(II) sulfide, copper carbonate, copper dodecanate, copper ethylacetoacetate, copper fluoride, copper oxalate, copper perchlorate, copper pyrophosphate, copper selenate, copper stearate, copper tartrate, copper xanthate, etc.

Of these copper and copper salts, cupric salts (e.g., copper acetate, cupric chloride, and cupric bromide) are preferably used in the present invention.

Amines used in the present invention include N,N,N',N'-tetramethylethylenediamine, amidines (e.g., 1,8-diazabicyclo[5,4,0]-7-undecene, and 1,5-diazabicyclo[4,3,0]-5-nonene), amino acids (e.g., glycine, sarcocine, valine, leucine, isoleucine, serine, threonine, glutamic acid, lysine, arginine, histidine, phenylalanine, tyrosine, triptophane, proline, and hydroxyproline), and pyridines (e.g., pyridine, α-picoline, β-picoline, γ-picoline, 2,6-lutidine, 2,4-lutidine, 2,3-lutidine, 2,5-lutidine, 3,5-lutidine, 3,4-lutidine, 2,4,6-collidine, 4-dimethylaminopyridine, 2-dimethylaminopyridine, 2-picolinic acid, 2,2'-dipyridyl, 2,2'-dipyridylamine, 2,2'-dipyridylmethane, 2,2'-dipyridylketone, quinoline, 2-methylquinoline, 3-methylquinoline, 4-methylquinoline, 8-hydroxyquinoline, isoquinoline, 2,2':6',2''-terpyridyl, 2,2'-diquinolyl, 1,1'-diisoquinolyl, 3,3'-diisoquinolyl, 2-aminopyridine, 1-aminoisoquinoline, 2-aminoquinoline, acridine, 9-methylacridine, 1,10-phenanthroline, 2,4-dimethyl-1,10-phenanthroline, 2,4,6-tri-2-pyridyl-1,3,5-triazine, 2,9-dimethyl-1,10-phenanthroline, and 2,4,7,9-tetramethyl-1,10-phenanthroline).

As amines for use in the present invention, tertiary amines are preferable. Tertiary amines having

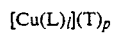

moiety in their structure may be used more preferably. Particularly preferable amines include ligands which have a pyridine residue, including ligands which have a pyridine residue, including bidentate ligands such as bipyridyl and 8-hydroxyquinoline.

As a base used in the present invention, use can be made of any base that is used in usual organic reactions. Preferable bases are strong bases whose conjugated acids have a dissociation constant (pKa) of 9 or more in water. Examples of the bases are alkali metal compounds or alkali earth metal compounds such as sodium hydroxide, potassium hydroxide, lithium hydroxide, sodium carbonate, potassium carbonate, lithium carbonate, sodium hydrogencarbonate, potassium hydrogencarbonate, sodium hydride, potassium hydride, lithium hydride, sodium amide, calcium oxide, barium oxide, and potassium t-butoxide; guanidine; 1,8-diazabicyclo[5,4,0]-7-undecene (DBU); and 1,5-diazabicyclo[4,3,0]-5-nonene (DBN). Bases preferably used in the present invention are, for example, sodium hydroxide, potassium hydroxide, sodium carbonate, potassium carbonate, sodium hydride, and DBU. When $R_3OH$ is a phenol compound, and when sodium hydroxide or potassium hydroxide is used as a base, it is preferable to prepare previously a phenoxide and to remove the water formed.

In the practice of the present invention, although an amine and copper or a copper compound may be added to the reaction system separately, they may be added simultaneously as a copper complex previously prepared as a copper complex of an amine. Particularly preferable complexes used as copper complexes in the present invention are those represented by the following formula (XIV):

$$[Cu(L)_l](T)_p \qquad \text{Formula(XIV)}$$

In formula (XIV), L represents an amine that is described above, l is an integer of 1 to 4, T represents an anion or a covalent-bond-forming moiety of the complex, p is a number required for balancing the charges of Cu and T (e.g., $\frac{1}{2}$, 1, and 2, and more particularly, for example, p is 2 if Cu is divalent and T is a monovalent anion), and when p is 2 or over, the T's may be the same or different. The copper complex used in the present invention may be in the form of a double salt formed by combining a copper complex represented by formula (XIV) with outer salts that are different. Examples of T are given below in the form of anions: $F^-$, $C^-$, $Br^-$, $I^-$, $ClO_4^-$, $BF_4^-$, $CH_3COO^-$, $NO_2^-$, $NO_3^-$, $N_3^-$, $SCN^-$, $OH^-$, $CN^-$, $SO_4^{2-}$, $SO_3^{2-}$, $HSO_4^-$, $HSO_3^-$, $NaSO_4^-$, $NaSO_3^-$, and $CO_3^{2-}$.

Examples of the complex used in the present invention include the following:

$(Cu(py)_2)Cl_2$
$(Cu(py)_2)Br_2$
$(Cu(bpy))Cl_2$
$(Cu(bpy))Br_2$
$(Cu(bpy)_2)Cl_2$
$(Cu(bpy)_2)Cl(ClO_4^-)$
$(Cu(bpy)_2)I_2$
$(Cu(bpy))(NO_3)_2$
$(Cu(bpy)_2)(NO_3)_2$
$(Cu(bpy)_3)(NO_3)_2$
$(Cu(bpy))(SCN)_2$
$(CuCl_2(terp))$
$(Cu(phen)_2)Cl_2$
$(Cu(phen)_2)(ClO_4)$
$(Cu(phen)_3)(ClO_4)_2$
$(cu(phen)_2)NO_3$
$(Cu(phen)_3)(NO_3)_2$ (py=pyridine, bpy=2,2'-bipyridyl, phen=1,10-phenanthroline, and terp=2,2':6',2''-terpyridyl)

These copper complexes can be easily produced by mixing the corresponding copper salt and the corresponding pyridine in water or an alcohol-based solvent. Methods of synthesizing these complexes and properties of these complexes are discussed in detail in "Mukikagobutsu no Gosei III," Shin Jikkenkagaku Koza, Vol. 8 (Maruzene Kabushiki-kaisha).

The reaction conditions of the reaction of the present invention will now be described in detail.

The molar ratio of the alcohol to the reaction substrate, i.e., the halogenobenzene compound in the present invention, is 0.1:1 to 1,000:1, preferably 1.0:1 to 200:1, and more preferably 10:1 to 100:1.

The molar ratio of the phenol compound to the reaction substrate, i.e., the halogenobenzene compound in the present invention, is 0.1:1 to 100:1, preferably 0.5:1 to 10:1, and more preferably 0.9:1 to 2.0:1.

The molar ratio of the copper, the copper compound, or the copper complex to the reaction substrate in the present invention is $1.0 \times 10^{-10}:1$ to 10:1, preferably $1.0 \times 10^{-6}:1$ to 1.0:1, and more preferably $1.0 \times 10^{-3}:1$ to 0.1:1.

The molar ratio of the amine to the reaction substrate in the present invention is $1.0 \times 10^{-10}:1$ to 1,000:1, preferably $1.0 \times 10^{-6}:1$ to 200:1, and more preferably $1.0 \times 10^{-3}:1$ to 100:1.

The molar ratio of the base to the reaction substrate is 0.1:1 to 100:1, preferably 0.5:1 to 10:1, and more preferably 1.0:1 to 3.0:1.

When the amine is a strong base such as DBU, DBN, and guanidine, the amine can be used as the base, and in that case, the molar ratio of the amine to the reaction substrate corresponds to that of the base to the reaction substrate. Herein the term "a strong base" refers to a base whose conjugated acid has a dissociation constant (pKa) of 9 or more in water. When the amine for use in the present invention is not a strong base, it is required to further use a strong base.

As the solvent in the reaction of the present invention can be mentioned, for example, acetonitrile, N,N-dimethylformamide, N,N-dimethylacetamide, dimethylsulfoxide, N-methylpyrrolidone, tetrahydrofuran, dioxane, dimethoxyethane, diglyme, ether, hexamethylphosphoryltriamide, sulfolane, diethyl carbonate, and 1,3-dimethyl-2-imidazolidone, although it is more preferable to permit an excess of the alcohol or the amine (e.g., pyridine, α-picoline, β-picoline, γ-picoline, quinoline, 2,6-lutidine, 2,4,6-collidine, N,N,N',N'-tetramethylethylenediamine, DBU, and DBN) that will be used in the reaction also to serve as a solvent.

The reaction temperature is $-78°$ C. to $200°$ C., preferably $-20°$ C. to $100°$ C., and more preferably $-10°$ C. to $60°$ C.

Specific Examples of Compounds

Specific examples of compounds to which the reaction of the present invention will be applied are shown below as combinations of compounds represented by formulae (I) and (II), although the present invention is not limited to them.

$$\underset{(I)}{\overset{R_1N}{\underset{H}{\bigvee}}\underset{2}{\overset{3}{\bigcirc}}\underset{6}{\overset{4}{(R_2)_m}}} + R_3OH \longrightarrow \underset{(II)}{\overset{R_1N}{\underset{H}{\bigvee}}\underset{2}{\overset{3}{\bigcirc}}\underset{6}{\overset{4}{(R_2)_m}}}$$

| $R_1$ | $R_2$ | X | $R_3$OH | Compound No. of Alkoxy compound (represented by formula (II)) |
|---|---|---|---|---|
| $CH_3CO-$ | (2)-$CH_3$-(4)-$CH_3$ | Br | $CH_3OH$ | (1) |
| " | (3)-$NHCOCH_3$-(4)-$NO_2$ | " | " | (2) |
| " | (2)-$CF_3$-(4)-Cl | " | " | (3) |
| " | (2)-$NO_2$-(4)-$CH_3$ | " | " | (4) |
| " | (3)-$NO_2$-(4)-$CH_3$ | " | " | (5) |
| " | (2)-$SO_3Na$-(4)-$NO_2$ | " | " | (6) |
| " | (2)-Cl-(4)-Cl | " | " | (7) |
| " | (3)-$CH_3$-(4)-$CH_3$ | " | " | (8) |
| " | (4)-$SO_2NH_2$ | " | " | (9) |
| " | (4)-$CO_2CH_3$ | " | " | (10) |
| " | (4)-$SO_2C_3H_7$ | " | " | (11) |
| " | (4)-$CH_2CO_2H$ | " | " | (12) |
| $CH_3CO-$ | (4)-Cl | Br | $CH_3OH$ | (13) |
| " | (2)-Cl-(5)-Cl | " | " | (14) |
| " | (2)-Cl-(4)-$NO_2$ | " | " | (15) |
| " | (4)-CN | " | " | (16) |
| " | (2)-$SO_2CH_3$-(4)-$NO_2$ | " | " | (17) |
| " | (3)-Cl-(4)-Cl | " | " | (18) |
| " | (4)-$OCH_3$ | " | " | (19) |
| " | (4)-$NHCOCH_3$ | " | " | (20) |
| " | (4)-$SO_3H$ | " | " | (21) |
| " | (3)-$CH_3$-(4)-$SO_3H$ | " | " | (22) |
| " | (3)-$SO_3H$-(4)-Cl | " | " | (23) |
| " | (3)-$CO_2H$-(4)-Cl | " | " | (24) |
| " | (4)-$SO_2NH$-⟨thiazole⟩ | " | " | (25) |
| " | (4)-$SO_2NH$-⟨pyrimidine⟩ | " | " | (26) |
| $CH_3CO-$ | (2)-OH-(3)-$NO_2$-(5)-$NO_2$ | Br | $CH_3OH$ | (27) |
| " | (2)-OH-(5)-Cl | " | " | (28) |
| " | (3)-Cl-(4)-OH | Br | " | (29) |
| " | (2)-OH-(4)-$NO_2$ | " | " | (30) |

-continued $$\underset{(I)}{\overset{R_1N}{\underset{H}{\bigvee}}\overset{3}{\underset{2}{\bigvee}}\overset{4}{\underset{1}{\bigvee}}\overset{(R_2)_m}{\underset{6}{\bigvee}}} + R_3OH \longrightarrow \underset{(II)}{\overset{R_1N}{\underset{H}{\bigvee}}\overset{3}{\underset{2}{\bigvee}}\overset{4}{\underset{1}{\bigvee}}\overset{(R_2)_m}{\underset{6}{\bigvee}}}$$

| $R_1$ | $R_2$ | X | $R_3OH$ | Compound No. of Alkoxy compound (represented by formula (II)) |
|---|---|---|---|---|
| " | (2)-OH-(4)-$NO_2$-(5)-Cl | " | " | (31) |
| " | (2)-OH-(4)-$NO_2$-(5)-O—⟨phenyl⟩ | " | " | (32) |
| " | (4)-$NO_2$ | " | " | (33) |
| " | (4)-$N(C_2H_5)_2$ | " | " | (34) |
| " | (4)-$N(CH_3)_2$ | " | " | (35) |
| " | (2)-$CH_3$-4-$N(CH_3)_2$ | " | " | (36) |
| " | (4)-$NHNHCOC_5H_{11}$ | " | " | (37) |
| " | (2)-Cl-(4)-$SO_3Na$-(5)-Cl | " | " | (38) |
| " | (4)-$CO_2H$ | " | " | (39) |
| " | (3)-$CO_2H$-(4)-OH | " | " | (40) |
| " | (4)-NHCOCHO—⟨2-$C_4H_9$, 4-$C_5H_{11}(t)$⟩ | " | " | (41) |
|  |  |  |  |  |
| $CH_3CO—$ | (4)-$SO_2N$—⟨$CH_3$, $C_{18}H_{37}$⟩ | Br | $CH_3OH$ | (42) |
| " | (3)-$NHCOC_{13}H_{27}$-(4)-$OCH_3$ | " | " | (43) |
| " | (3)-$OCH_3$-(4)-$NHCOC_5H_{11}$ | " | " | (44) |
| " | (4)-$COCH_2CONH$—⟨2-$OCH_3$⟩ | " | " | (45) |
|  |  |  |  |  |
| " | (2)-$OCH_3$-(4)-$NO_2$-(5)-$OCH_3$ | " | " | (46) |

-continued
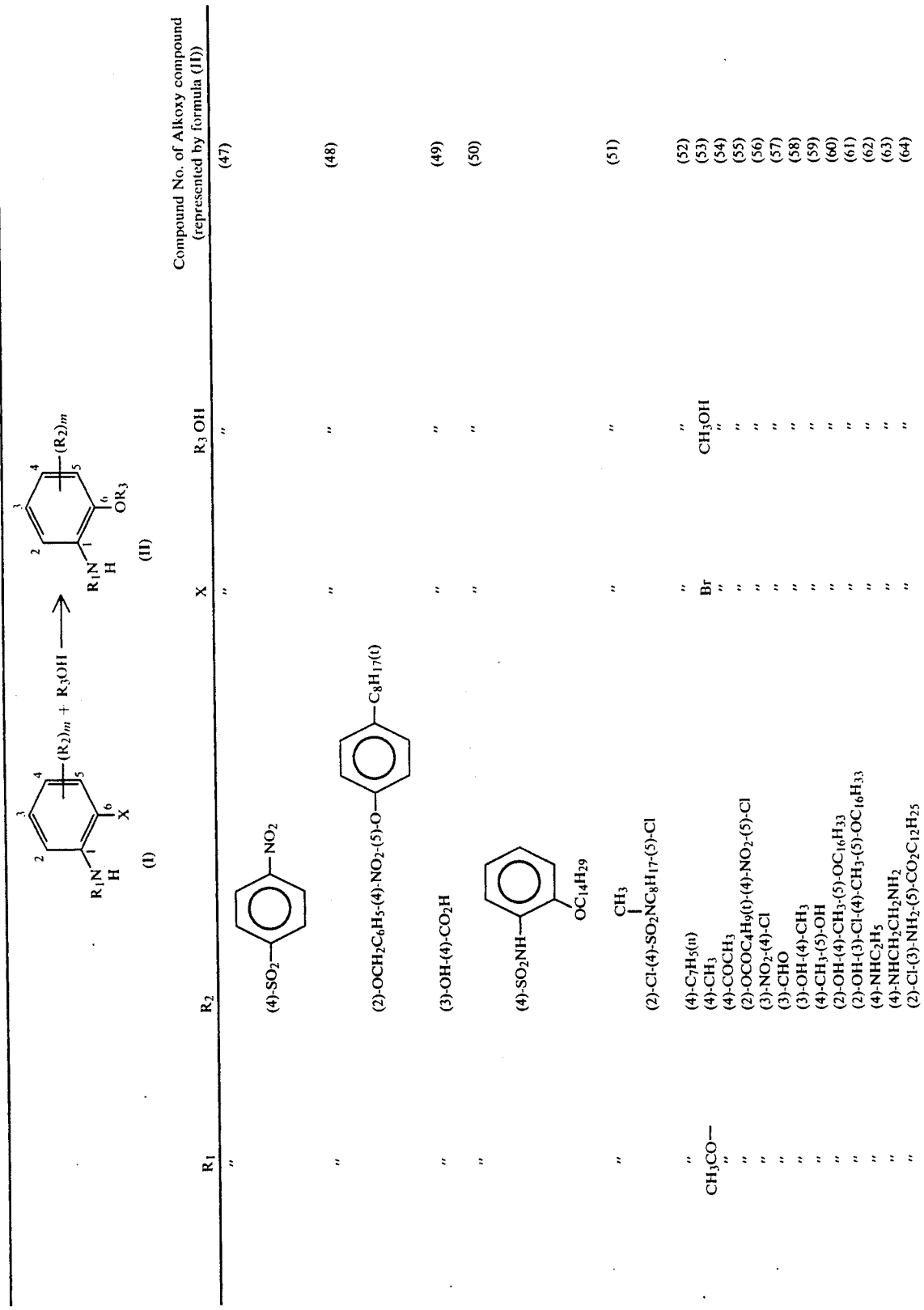
| R₁ | R₂ | X | R₃OH | Compound No. of Alkoxy compound (represented by formula (II)) |
|---|---|---|---|---|
| " | (4)-SO₂- ⌬ -NO₂ | " | " | (47) |
| " | (2)-OCH₂C₆H₅-(4)-NO₂-(5)-O- ⌬ -C₈H₁₇(t) | " | " | (48) |
| " | (3)-OH-(4)-CO₂H | " | " | (49) |
| " | (4)-SO₂NH- ⌬ -OC₁₄H₂₉ | " | " | (50) |
| " | (2)-Cl-(4)-SO₂N(CH₃)C₈H₁₇-(5)-Cl | " | " | (51) |
| CH₃CO— | (4)-C₇H₁₅(n) | Br | CH₃OH | (52) |
| " | (4)-CH₃ | " | " | (53) |
| " | (4)-COCH₃ | " | " | (54) |
| " | (2)-OCOC₄H₉(t)-(4)-NO₂-(5)-Cl | " | " | (55) |
| " | (3)-NO₂-(4)-Cl | " | " | (56) |
| " | (3)-CHO | " | " | (57) |
| " | (3)-OH-(4)-CH₃ | " | " | (58) |
| " | (4)-CH₃-(5)-OH | " | " | (59) |
| " | (2)-OH-(4)-CH₃-(5)-OC₁₆H₃₃ | " | " | (60) |
| " | (2)-OH-(3)-Cl-(4)-CH₃-(5)-OC₁₆H₃₃ | " | " | (61) |
| " | (4)-NHC₂H₅ | " | " | (62) |
| " | (4)-NHCH₂CH₂NH₂ | " | " | (63) |
| " | (2)-Cl-(3)-NH₂-(5)-CO₂C₁₂H₂₅ | " | " | (64) |

-continued $$\begin{array}{c} \underset{R_1N}{\overset{H}{\underset{1}{\bigvee}}} \underset{6}{\overset{5}{\underset{4}{\bigvee}}} (R_2)_m + R_3OH \longrightarrow \underset{R_1N}{\overset{H}{\underset{1}{\bigvee}}} \underset{6}{\overset{5}{\underset{4}{\bigvee}}} (R_2)_m \\ (I) \hspace{3cm} (II) \end{array}$$

| $R_1$ | $R_2$ | X | $R_3$OH | Compound No. of Alkoxy compound (represented by formula (II)) |
|---|---|---|---|---|
| " | (3)-OH-(4)-NHCONH—⟨C₆H₄⟩-Cl | " | " | (65) |
| " | (2)-Cl-(4)-NHCONH—⟨C₆H₃⟩-CN-(5)-OH | " | " | (66) |
| CH₃CO— | (4)-CH₃-(5)-CH₃ | Br | CH₃OH | (67) |
| " | (2)-OCH₃-(4)-C₄H₉(t)-(5)-OC₁₂H₂₅ | " | " | (68) |
| " | (2)-Cl-(4)-Cl-(5)-OC₁₄H₂₉ | " | " | (69) |
| " | (4)-C₁₂H₂₅ | " | " | (70) |
| " | (4)-C₁₆H₃₃ | " | " | (71) |
| " | (3)-Cl-(4)-CH₃ | " | " | (72) |
| " | (4)-SO₂NH—⟨pyrimidine-CH₃,CH₃⟩ | " | " | (73) |
| " | (4)-Br | " | " | (74) |
| " | (4)-CH₂CH₂—⟨C₆H₃⟩-OH,OH | " | " | (75) |
| " | (3)-OCH₃-(4)-OCH₃ | " | " | (76) |
| " | (3)-OH-(4)-CHO | " | " | (77) |

-continued $$\underset{(I)}{\overset{R_1N}{\underset{H}{\bigvee}}\underset{X}{\overset{(R_2)_m}{\bigvee}}} + R_3OH \longrightarrow \underset{(II)}{\overset{R_1N}{\underset{H}{\bigvee}}\underset{OR_3}{\overset{(R_2)_m}{\bigvee}}}$$

| R₁ | R₂ | X | R₃OH | Compound No. of Alkoxy compound (represented by formula (II)) |
|---|---|---|---|---|
| " | (3),(4)-O-CH₂-O- | " | " | (78) |
| " | (3),(4)-O-CH₂CH₂-O- | " | " | (79) |
| CH₃CO— | (4),(5)-O-CH₂-O- | Br | CH₃OH | (80) |
| " | (4)-OH | " | " | (81) |
| " | (4)-NH—C₆H₄—OCH₃ | " | " | (82) |
| " | (4)-NH—C₆H₄—OH | " | " | (83) |
| " | (4)-OC₁₆H₃₃ | " | " | (84) |
| " | (4)-N(C₂H₅)(C₂H₄OH) | " | " | (85) |
| " | (4)-N(C₂H₅)(C₂H₄NHSO₂CH₃) | " | " | (86) |
| " | (2)-NHCOCH₃-(4)-CH₃-(5)-CH₃ | " | " | (87) |
| " | (4)-NH₂ | " | " | (88) |

-continued $$\underset{(I)}{\underset{R_1N}{\overset{H}{\bigvee}}\text{-}X} + R_3OH \longrightarrow \underset{(II)}{\underset{R_1N}{\overset{H}{\bigvee}}\text{-}OR_3}$$

| R₁ | R₂ | X | R₃OH | Compound No. of Alkoxy compound (represented by formula (II)) |
|---|---|---|---|---|
| " | (4)-NH-phenyl | " | " | (89) |
| " | (2)-NO₂-(4)-NO₂ | " | " | (90) |
| " | (4)-I | " | " | (91) |
| CH₃CO— | (4)-phenyl | Br | CH₃OH | (92) |
| " | (3)-Cl-(4)-OH-(5)-Cl | " | " | (93) |
| " | (3),(4)-benzoyl | " | " | (94) |
| " | (4)-CH₂CH₂OH | " | " | (95) |
| " | (4)-CH(OH)-COOH-phenyl | " | " | (96) |
| " | (2)-OH-(4)-CH₃-(5)-OCH₃ | " | " | (97) |
| " | (2)-OH-(4)-C₈H₁₇-(t)-(5)-OC₁₆H₃₃ | " | " | (98) |
| " | (3)-CH₃-(4)-OH-(5)-CH₃ | " | " | (99) |

-continued $$\underset{(I)}{\overset{R_1N}{\underset{H}{\bigwedge}}\phantom{x}\overset{(R_2)_m}{\bigcirc}\phantom{x}X} + R_3OH \longrightarrow \underset{(II)}{\overset{R_1N}{\underset{H}{\bigwedge}}\phantom{x}\overset{(R_2)_m}{\bigcirc}\phantom{x}OR_3}$$

| R₁ | R₂ | X | R₃OH | Compound No. of Alkoxy compound (represented by formula (II)) |
|---|---|---|---|---|
|  | (4)- pyrazolonyl | " | " | (100) |
| " | (3),(4)- triazolyl-NH | " | " | (101) |
| " | (4)-F | " | " | (102) |
| CH₃CO— | (3),(4)- methoxyethylamino | Br | CH₃OH | (103) |
| " | (2)-NHCOCH₃-(4)-Cl-(5)-Cl | " | " | (104) |
| " | (2)-Cl-(4)-Cl-(5)-Cl | " | " | (105) |
| " | (4)-CF₃ | " | " | (106) |
| " | (2)-NO₂-(4)-OC₁₂H₂₅ | " | " | (107) |
| " | (2)-NO₂-(4)-CF₃ | " | " | (108) |
| " | (2)-OCH₃-(4)-NO₂-(5)-OCH₃ | " | " | (109) |
| " | (4)-CONH-C₆H₄-OC₁₂H₂₅ | " | " | (100) |
| " | (2)-CH₃-(4)SO₃H-(5)-CH₃ | " | " | (111) |
| " | (3)SO₃H-(4)-OCH₂CH₂OCH₃ | " | " | (112) |
| " | (4)-N=N-C₆H₄-SO₃Na | " | " | (113) |

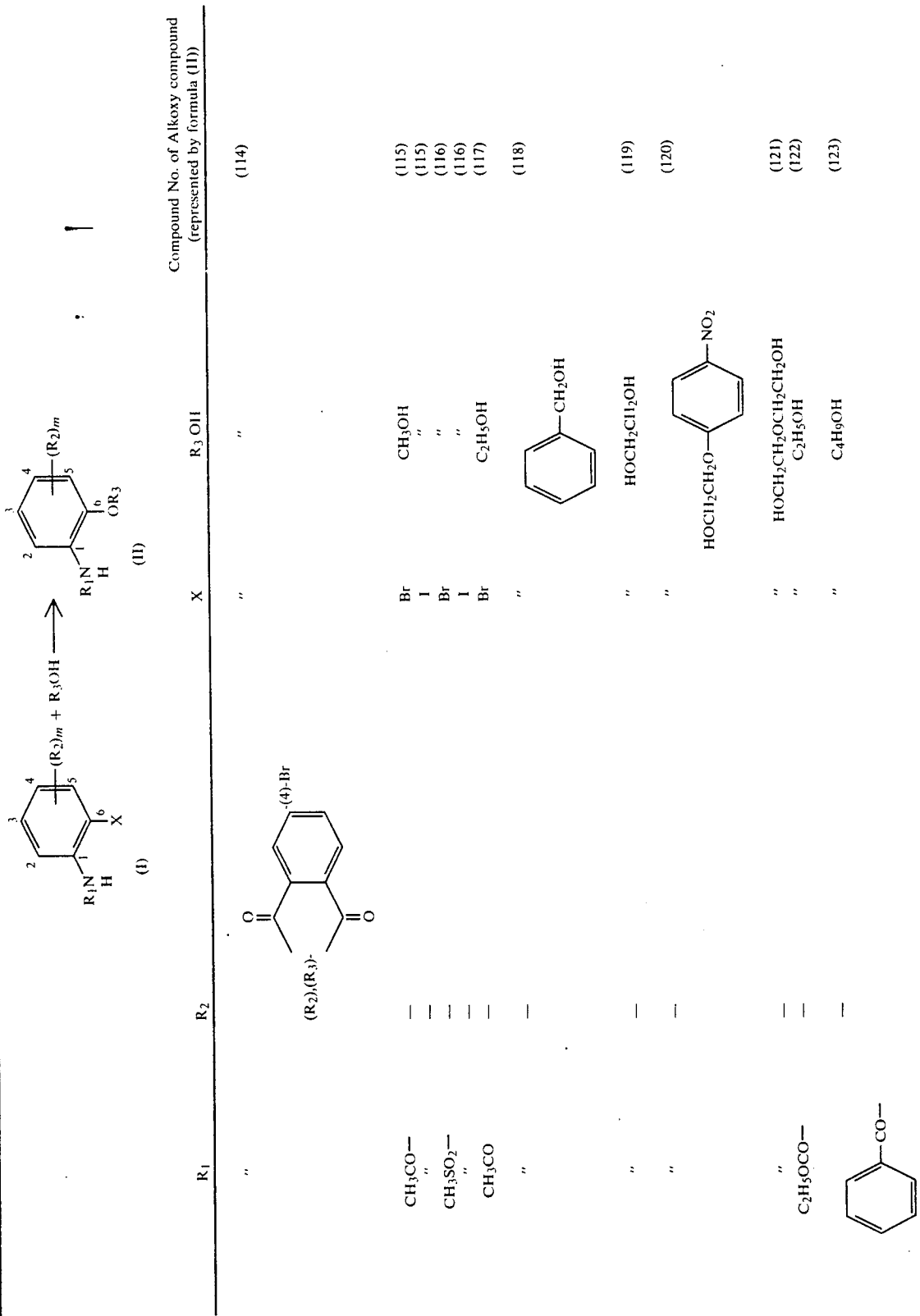

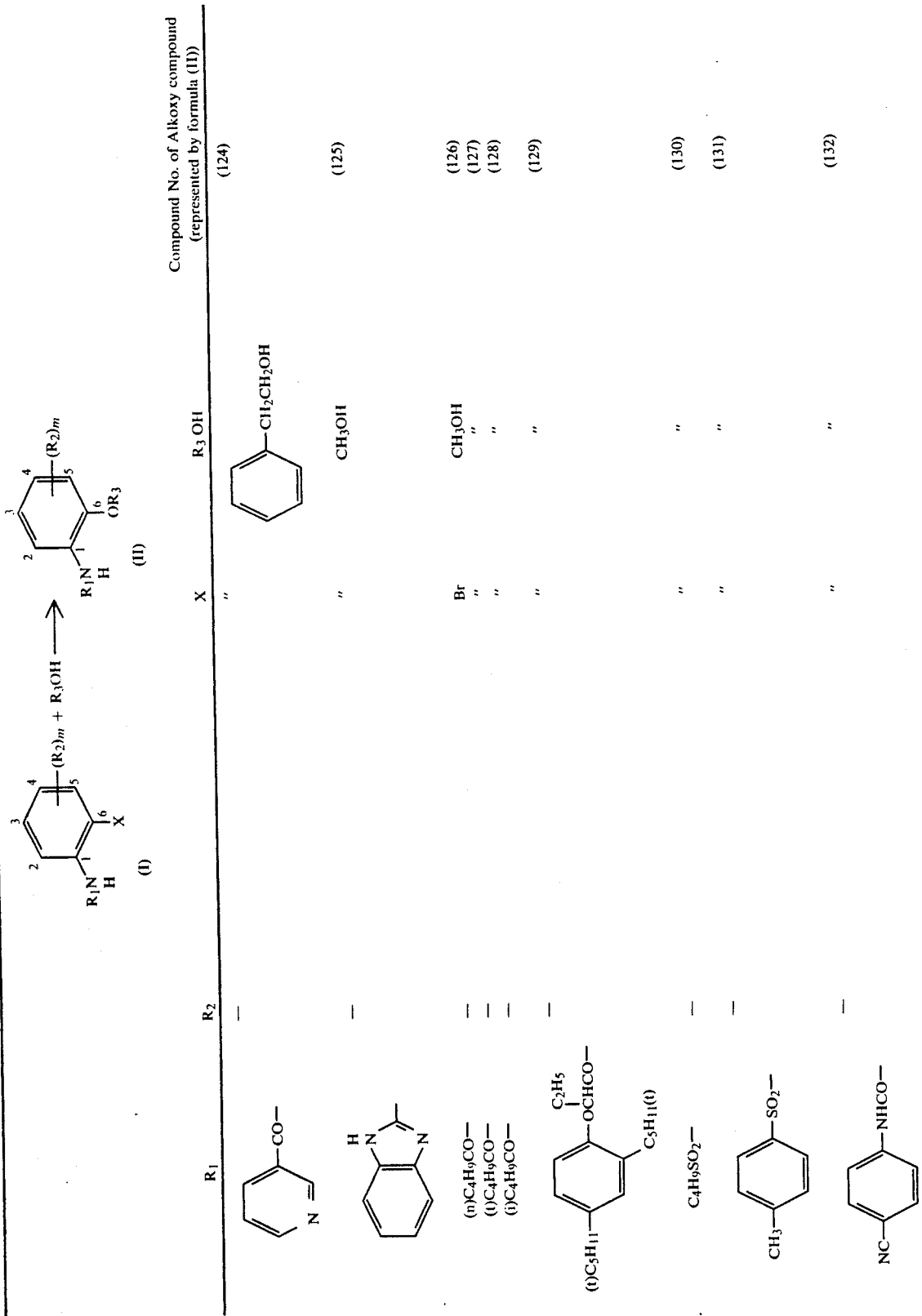

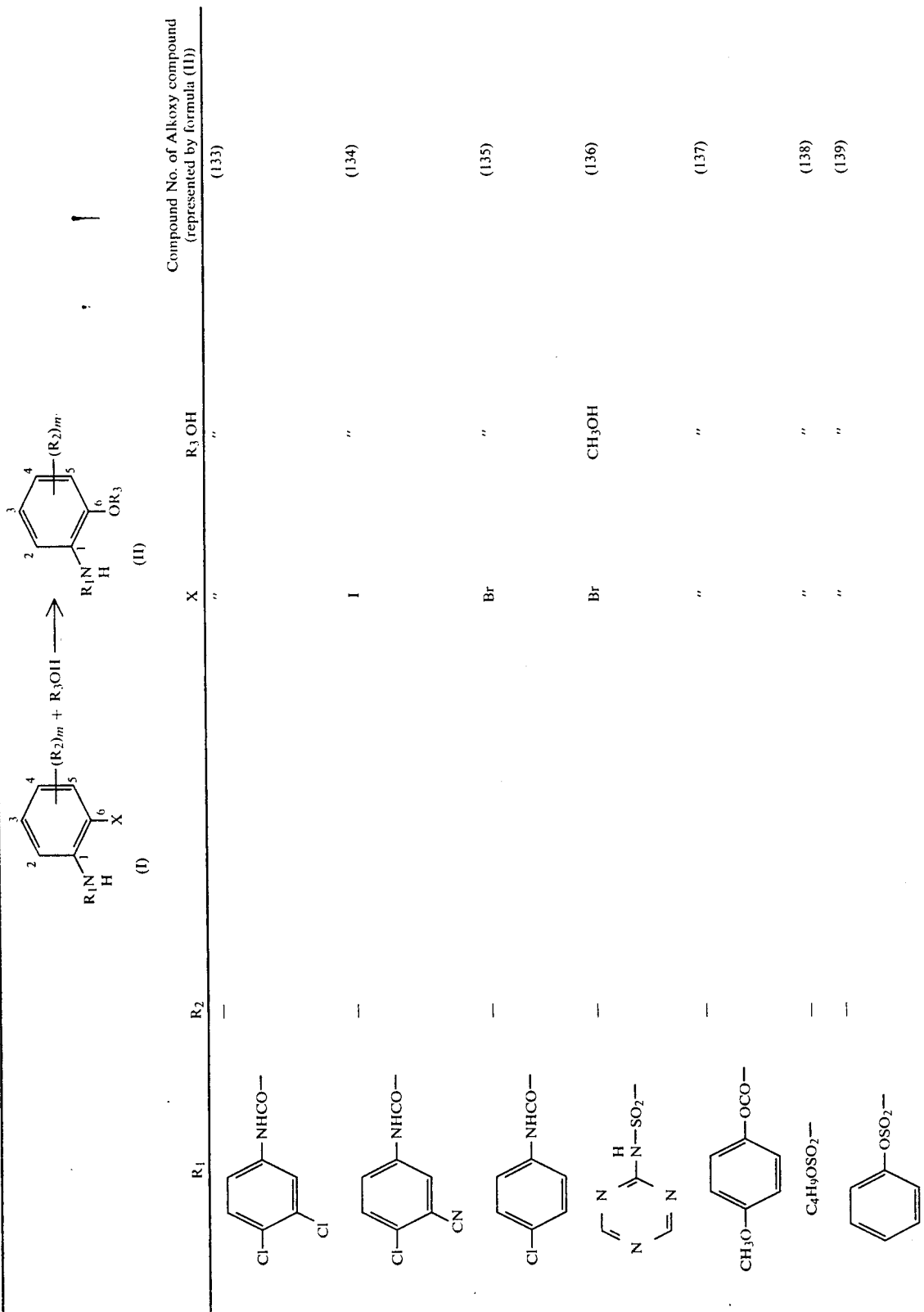

-continued
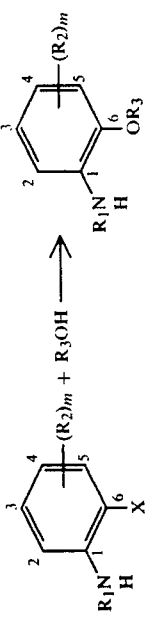
| $R_1$ | $R_2$ | X | $R_3OH$ | Compound No. of Alkoxy compound (represented by formula (II)) |
|---|---|---|---|---|
| $CH_3CO-$ | (2),(3)-(4)-$SO_3Na$ | " | " | (140) |
| " | (3)-$SO_3Na$-(4),(5) $SO_3Na$ | " | $C_2H_5OH$ | (141) |
| (t)-$C_4H_9CO-$ | (2),(3)-(4)-$SO_3Na$ $SO_3Na$ | " | " | (142) |
Note: In the column $R_2$, the number in parentheses shows the position where each group is introduced.

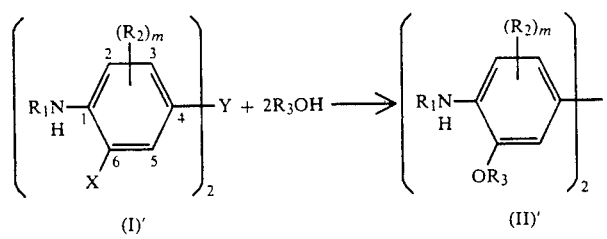

| $R_1$ | $R_2$ | X | Y | $R_3$OH | Number |
|---|---|---|---|---|---|
| $CH_3CO-$ | (2)-$OCH_3$ | Br | (Single bond) | $C_2H_5OH$ | (143) |
| " | (2)-$CH_3$ | " | — | " | (144) |
| $CH_3SO_2-$ | — | " | $-SO_2-$ | " | (145) |
| " | — | " | — | $CH_3OH$ | (146) |
| $CH_3OCO-$ | — | " | $-O-$ | " | (147) |
| $(i)C_4H_9OCO-$ | — | " | $-\underset{\underset{O}{\parallel}}{C}-$ | " | (148) |
| $C_2H_5OCO-$ | — | " | $-\underset{\underset{S}{\parallel}}{C}-$ | " | (149) |
| $C_4H_9SO_2-$ | (3)-$SO_3Na$ | " | $-CH=CH-$ | $HOCH_2CH_2OH$ | (150) |
| ⌬-$SO_2-$ | — | " | $-\underset{\underset{\text{⌬}}{\mid}}{N}-$ | " | (151) |
| Cl-⌬-$SO_2-$ | — | " | $-\underset{\underset{H}{\mid}}{N}-$ | $HOCH_2CH_2OCH_3$ | (152) |
| ⌬-$CO-$ | — | " | $-S-$ | " | (153) |
| ⌬-$CH_2CO-$ | — | " | $-S-S-$ | $HOCH_2CH_2O$-⌬-$NO_2$ | (154) |
| $CH_3O$-⌬-$CO-$ | — | " | $-\underset{\underset{CH_3}{\mid}}{N}-$ | $HO(CH_2CH_2O)_2H$ | (155) |

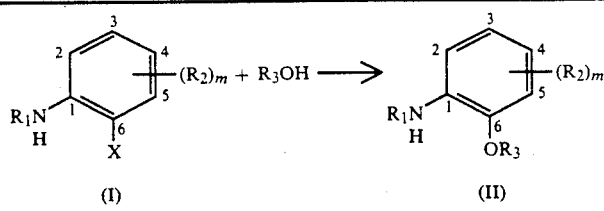
| R₁ | R₂ | X | R₃OH | Compound No. of Aryloxy compound (represented by formula (II)) |
|---|---|---|---|---|
| CH₃CO | — | Br | Cl—⬡—OH | (156) |
| " | — | " | Br—⬡—OH | (157) |
| " | — | " | ⬡—OH | (158) |
| " | — | " | CH₃—⬡—OH | (159) |
| " | — | " | C₄H₉—⬡—OH | (160) |
| " | — | " | (t)C₈H₁₇—⬡—OH | (161) |
| " | — | " | CH₃O—⬡—OH | (162) |
| " | — | " | C₄H₉O—⬡—OH | (163) |
| CH₃CO | — | Br | ⬡—CH₂O—⬡—OH | (164) |
| " | — | " | C₈H₁₇\N—⬡—OH / CH₃ | (165) |
| " | — | " | ⬡—OH (2,3-di-Cl) | (166) |

-continued
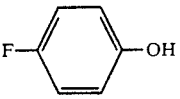
| R₁ | R₂ | X | R₃OH | Compound No. of Aryloxy compound (represented by formula (II)) |
|---|---|---|---|---|
| " | — | " | 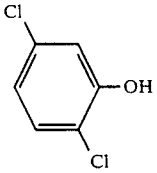 4-F-C₆H₄-OH | (167) |
| " | — | " | 2,5-Cl₂-C₆H₃-OH | (168) |
| " | — | " | 3-CH₃-C₆H₄-OH | (169) |
| " | — | " | 3-C₁₅H₃₁-C₆H₄-OH | (170) |
| " | — | " | 3,5-(CH₃)₂-4-Cl-C₆H-OH | (171) |
| CH₃CO | — | Br | 3-CH₃O-C₆H₄-OH | (172) |
| " | — | " | 3-(CH₃)₂N-C₆H₄-OH | (173) |
| " | (2)-CH₃-(4)-CH₃ | " | 4-CH₃O-C₆H₄-OH | (174) |
| C₂H₅OCO | (2)CF₃-(4)-Cl | " | 4-CH₃-C₆H₄-OH | (175) |

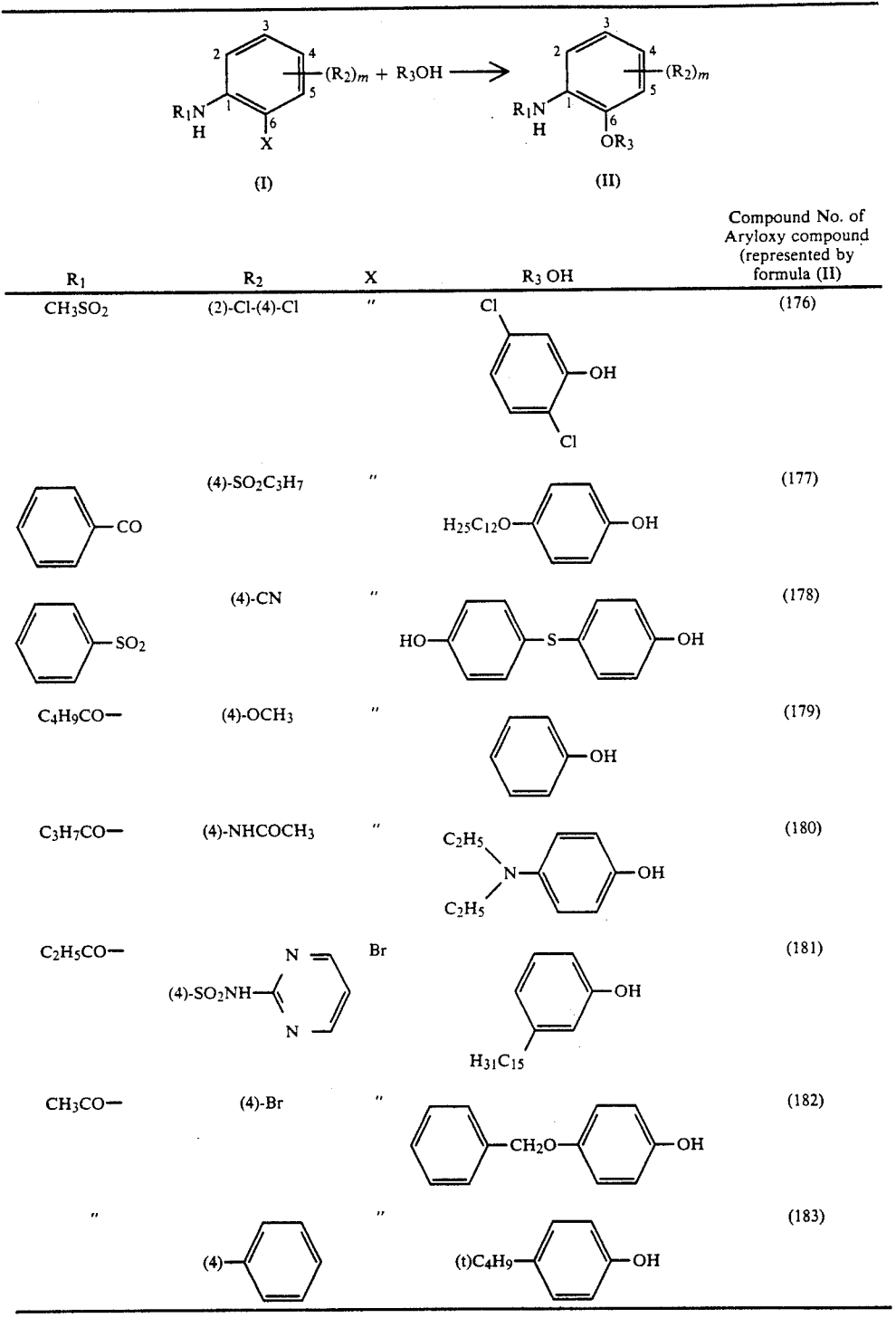

According to the present invention, an alkoxybenzene compound or an aryloxybenzene compound can be produced under moderate conditions in good yield with high selectivity.

The present invention will now be described in further detail with reference to the following Examples.

EXAMPLE 1

Synthesis of 2-acetamidoanisole (Compound No. 115)

2-Bromo-1-acetylaminobenzene was synthesized in the usual manner from 2-bromoaniline. That is, 150 ml of acetonitrile was added to 25.0 g of 2-bromoaniline, then 15.1 ml of glacial acetic acid was added thereto, and the reaction mixture was heated under reflux for 2 hours. After bringing its temperature to room temperature, 300 ml of ethyl acetate was added thereto, and after the resulting mixture was washed with water twice, the solvent was distilled off, and recrystallization of the crude crystals from a hexane/ethyl acetate solvent mixture was carried out, to obtain 23.2 g (yield: 75%) of 2-bromo-1-acetylaminobenzene.

Then, 2.14 g of the 2-bromo-1-acetylaminobenzene was added to a solution containing 2.3 ml of a 28% methanol solution of sodium methoxide, 100 mg of cuprous chloride, and 145 mg of 8-hydroxyquinoline in 40 ml of methanol, and the mixture was heated under reflux for 50 minutes. After cooling with water, ethyl acetate was added thereto, and the resulting mixture was washed with water and dried over Glauber's salt. The solvent was distilled off, and the obtained crude crystals were recrystallized from an n-hexane/ethyl acetate solvent mixture, to obtain 1.56 g (yield: 95%) of the desired compound. The spectrum data of the compound was in agreement with the spectrum data of the separately synthesized reference compound.

In the case wherein 2-iodo-1-acetylaminobenzene was used instead of 2-bromo-1-acetylaminobenzene, the desired compound (115) was obtained in a yield of 93%.

EXAMPLE 2

Synthesis of 2-ethoxy-1-ethoxycarbonylaminobenzene (Compound No. 122)

The synthesis was carried out as follows by using 2-bromo-1-ethoxycarbonylaminobenzene prepared in a usual manner.

2.44 g of the 2-bromo-1-ethoxycarbonylaminobenzene was added to a solution containing 680 mg of sodium ethoxide, 170 mg of cupric chloride dihydrate, and 156 mg of 2,2'-bipyridine in 40 ml of methanol, and the mixture was heated under reflux for 1.5 hours. After the temperature was brought to room temperature, ethyl acetate was added thereto, and the resulting mixture was washed with water and dried over Glauber's salt. The solvent was distilled off, and the obtained crude crystals were recrystallized from a n-hexane/ethyl acetate solvent mixture, to obtain 1.75 g (yield: 84%) of the desired compound. The spectrum data of the compound was in agreement with the spectrum data of the separately synthesized reference compound.

EXAMPLE 3

Synthesis of 2-methanesulfonylaminoanisole (Compound No. 116)

The synthesis was carried out as follows using 2-bromo-1-methanesulfonylaminobenzene prepared in a usual manner.

2.50 g of 2-bromo-1-methanesulfonylaminobenzene was added to a solution containing 1.52 g of DBU, 85 g of cupric chloride dihydrate, and 90 mg of 1,10-phenanthroline in 40 ml of methanol, and the mixture was heated under reflux for 5 hours. After the temperature was brought to room temperature, the reaction mixture was treated in a usual manner, and crystallization was effected from n-hexane/ethyl acetate, to produce 1.64 g (yield: 82%) of the desired compound.

EXAMPLE 4

Synthesis of 2-acetamidoanisole (Compound No. 115) (under conditions different from those in Example 1)

2.3 ml of a 28% solution of sodium methoxide in methanol and 63 mg of copper powder were added to 40 ml of methanol, and the mixture was heated under reflux for 1 hour. Then, 145 mg of 8-hydroxyquinoline and 2.14 g of 2-bromo-1-acetylaminobenzene were added thereto, and the mixture was heated under reflux for 3 hours. The reaction mixture was treated in a usual manner, to obtain 1.43 g (yield: 87%) of the desired compound.

EXAMPLE 5

Synthesis of 2-(2-hydroxyethoxy)-1-acetylaminobenzene (Compound No. 119)

440 mg of sodium hydride solution (concentration 40%) was added portionwise to 30 ml of ethylene glycol. After abating of the froth occurred, 50 mg of cuprous chloride, 75 mg of 8-hydroxyquinoline and 1.07 g of 2-bromo-1-acetylamino-benzene were added to the solution and the mixture was heated at 70° to 80° C. for 50 minutes. The reaction mixture was treated in a usual manner, and then crystallization was effected from a solvent mixture of n-hexane and ethyl acetate to give 720 mg of the desired compound. Yield: 74%, melting point: 89°–91° C.

EXAMPLE 6

Alkoxy compounds No. 74 and No. 76 in the above table can be synthesized by the same procedure as in Example 1.

COMPARATIVE EXAMPLE 1

2.3 ml of methanol solution containing sodium methoxide (28%), 100 mg of cuprous chloride and 2.14 g of 2-bromo-1-acetylaminobenzene were added to 40 ml of methanol and the mixture was heated under reflux for 5 hours. It resulted in only the recovery of the starting materials.

Comparing the result in Example 1 with the result in comparative example 1, the effect of 8-hydroxyquinoline added is apparent.

COMPARATIVE EXAMPLE 2

2.3 ml of methanol solution containing sodium methoxide (28%), 100 mg of cuprous chloride, 262 mg of triphenyl phosphine and 2.14 g of 2-bromo-acetylaminobenzene were added to 40 ml of methanol and the mixture was heated under reflux for 5 hours. However it resulted in only the recovery of the starting materials.

Various phosphine system ligands other than triphenyl phosphine were tested, but no effect of those ligands added was observed.

EXAMPLE 7

Synthesis of compound No. 159

After dissolving 1.08 g of p-cresol and 2.14 g of o-bromo-acetoanilide in 20 ml of 1,3-dimethyl-2-imidazolidone, 0.88 g of sodium hydroxide was added dropwise to the solution. Then, 0.10 g of cuprous chloride and 0.15 g of 8-hydroxyquinoline were added to the solution, and the mixture was stirred at 90° to 95° C. of inner temperature thereof for 2 hours in an atmosphere of nitrogen. To the resulting mixture, ethyl acetate and diluted hydrochloric acid solution were added, then the organic layer was separated and dried over Glauber's salt. The oily product obtained after evaporation of solvent was purified by the use of a silica gel column chromatography to obtain 1.08 g compound No. 159. According to a $^1$H-NMR analysis, the reaction mixture had a composition of a ratio 64:5:31 in the desired compound No. 159:reductive dehalogenated compound:homo-coupling product (2,2'-acetylaminobiphenyl).

COMPARATIVE EXAMPLE 3

The same reaction procedure was repeated as in Example 7, except that an equimolar of bromobenzene is used in place of o-bromo-acetoanilid. However, it resulted only in the recovery of the starting materials.

COMPARATIVE EXAMPLE 4

After dissolving 1.08 g of p-cresol and 2.14 g of o-bromo-acetoanilide in 20 ml of 1.3-dimethyl-2-imidazolidone, 0.88 g of sodium hydroxide was added dropwise to the solution. Then, 0.15 g of 8-hydroxyquinoline was added to the solution, and the mixture was stirred at 90° to 95° C. of inner temperature thereof for 2 hours in an atmosphere of nitrogen. However, it resulted only in the recovery of the starting material.

COMPARATIVE EXAMPLE 5

After dissolving 1.08 g of p-cresol and 2.14 g of o-bromo-acetoanilide in 20 ml of 1.3-dimethyl-2-imidazolidone, 0.88 g of sodium hydroxide was added dropwise to the solution. Then, 0.10 g of cuprous chloride was added to the solution, and the mixture was stirred at 90° to 95° C. of inner temperature thereof for 2 hours in an atmosphere of nitrogen. However, it resulted in the formation of reductive dehalogenated compound and the compound No. 159 was not obtained at all.

In Example 7, when sodium hydroxide as a base was not added, compound No. 159 was not obtained at all.

COMPARATIVE EXAMPLE 6

A replacement reaction as in Example 7 was conducted by changing p-cresol ($\sigma_p = -0.17$, CH$_3$) to

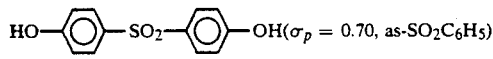

as phenol, but no desired reaction product was obtained while only a reductive dehalogenated compound and N-acetyl-N-(2-acetoamidophenyl)-2-bromo-aniline were obtained.

EXAMPLE 8

Synthesis of compound No. 159 (under the conditions different from those in Example 7)

After dissolving 1.08 g of p-cresol and 2.14 g of o-bromoacetoanilide in 20 ml of 1.3-dimethyl-2-imidazolidone, 3.0 ml of DBU, 0.17 g of cupric chloride dehydrate and 0.15 g of 8-hydroxyquinoline were added successively to the solution. The resulting mixture was stirred at 90° to 95° C. of inner temperature thereof for 10 hours in an atmosphere of nitrogen. After the temperature was brought to room temperature, the same post-treatment as in Example 7 was carried out to obtain 0.92 g of compound No. 159.

EXAMPLE 9

The other compounds can be synthesized by the same procedure as in Example 7 or Example 8.

Chemical shifts in $^1$H-NMR of the representative compounds of the present invention are shown below.

Compound No. 159 $^1$H-NMR(200 MHz), Solvent: CDCl$_3$, δ ppm: 8.45 (dd, 1H, J=8.0, 1.3 Hz), 7.76 (broad, s, 1H), 7.18 (d, 2H, J=8.7 Hz), 7.10 (ddd, 1H, J=8.0, 8.0, 1.3 Hz), 6.93 (ddd, 1H, J=8.0, 8.0, 1.3 Hz), 6.90 (d, 2H, J=8.7 Hz), 6.80 (dd, 1H, J=8.0 Hz), 2.38 (s, 3H), 2.20 (s, 3H).

Compound No. 182 $^1$H-NMR (200 MHz), Solvent: CDCl$_3$, δ ppm: 8.35 (d, 1H, J=8.7 Hz), 7.78 (broad, s, 1H), 7.50–7.30 (m, 5H), 7.16 (dd, 1H, J=8.7, 2.0 Hz), 7.02 (d, 2H, J=8.0 Hz), 6.98 (d, 2H, J=8.0 Hz), 6.81 (d, 1H, J=2.0 Hz), 5.08 (s, 2H), 2.20 (s, 3H).

Having described our invention as related to the embodiment, it is our intention that the invention not be limited by any of the details of the description, unless otherwise specified, but rather be construed broadly within its spirit and scope as set out in the accompanying claims.

What we claim is:

1. A process for producing an alkoxybenzene compound or an aryloxybenzene compound, which comprises reacting a halogenobenzene compound represented by formula (I) with an alcohol or a phenol compound represented by R$_3$OH in the presence of copper or a copper compound, a tertiary amine having

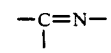

in its structure, and a base to obtain an alkoxybenzene compound or an aryloxybenzene compound represented by Formula (II):

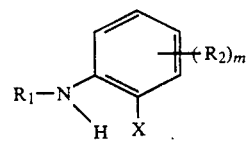

Formula (I)

wherein X represents a halogen atom, R$_1$ represents a heterocyclic residue, an acyl group, an alkylsulfonyl group, an arylsulfonyl group, a carbamoyl group, a sulfamoyl group, an alkoxycarbonyl group, an aryloxycarbonyl group, an alkoxysulfonyl group, or an aryloxysulfonyl group, R$_2$ represents a group that can be substituted onto an aromatic ring, m is an integer of 0 to 4, R$_1$ and R$_2$ may bond together to form a 5- to 7-membered ring, R$_2$ groups may bond together to form a 5- to 7-membered ring, and when m is 2 or over, R$_2$ groups may be the same or different,

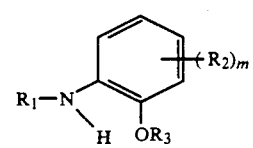

Formula (II)

wherein R$_1$, R$_2$ and m have the same meaning as in formula (I), and R$_3$ represents an alkyl group or an aryl group.

2. The process as claimed in claim 1, wherein the copper compound is a copper salt.

3. The process as claimed in claim 1, wherein the copper compound is a cupric salt.

4. The process as claimed in claim 1, wherein the amine is selected from the group consisting of N,N,N',N'-tetramethylenediamine, amidine, amino acid, and pyridine.

5. The process as claimed in claim 1, wherein the amine is a tertiary amine.

6. The process as claimed in claim 1, wherein the amine is a tertiary amine of a ligand having a pyridine residue.

7. The process as claimed in claim 1, wherein the base is one of whose conjugated acid has a dissociation constant of 9 or more in water.

8. The process as claimed in claim 1, wherein the base is selected from the group consisting of sodium hydroxide, potassium hydroxide, sodium carbonate, potassium carbonate, sodium hydride, and 1,8-diaza-bicyclo [5.4.0]-7-undesene.

9. The process as claimed in claim 1, wherein a copper complex of an amine is used in place of copper or a copper compound and an amine.

10. The process as claimed in claim 1, wherein the copper complex of an amine is a complex represented by formula (XIV) 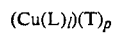

$$(Cu(L)_l)(T)_p$$

wherein L represents an amine, T represents an anion or a covalent bond forming moiety of the complex, l is an integer of 1 to 4, and p is a number required for balancing the charges of Cu and T.

11. The process as claimed in claim 1, wherein the molar ratio of the alcohol to the halogenobenzene compound is 0.1:1 to 1,000:1.

12. The process as claimed in claim 1, wherein the molar ratio of the phenol compound to the halogenobenzene compound is 0.1:1 to 100:1.

13. The process as claimed in claim 1, wherein the molar ratio of the copper, the copper compound or the copper complex to the halogenobenzene compound is $1.0 \times 10^{-10}$:1 to 10:1.

14. The process as claimed in claim 1, wherein the molar ratio of the amine to the halogenobenzene compound is $1.0 \times 10^{-10}$:1 to 1,000:1.

15. The process as claimed in claim 1, wherein the molar ratio of the base to the halogenobenzene compound is 0.1:1 to 100:1.

16. The process as claimed in claim 1, wherein the reaction temperature is $-78°$ C. to 200° C.

17. The process as claimed in claim 1, wherein an amine of a strong base is used as the base.

18. The process as claimed in claim 1, wherein an excess of the alcohol or the amine for the reaction is used as a solvent for the reaction.

19. The process as claimed in claim 1, wherein in Formula (I) $R_1$ is pyridine-3-yl, an acyl group having 1 to 36 carbon atoms, an alkylsulfonyl group having 1 to 36 carbon atoms, an arylsulfonyl having 6 to 36 carbon atoms, or an alkoxycarbonyl group having 2 to 36 carbon atoms.

20. The process as claimed in claim 1, wherein in formula (I), $R_2$ represents a halogen atom, an alkyl group having 1 to 18 carbon atoms, a carboxyl group, a sulfo group, a hydroxyl group, a cyano group, a carbamoyl group having 1 to 37 carbon atoms, a sulfamoyl having 0 to 36 carbon atoms, a carbonamido group having 1 to 36 carbon atoms, a sulfonamido group having 1 to 36 carbon atoms, an alkoxy group having 1 to 36 carbon atoms, an alkoxycarbonyl group having 2 to 36 carbon atoms, an amino group, a nitro group, or an acyl group having 1 to 24 carbon atoms.

21. The process as claimed in claim 1, wherein in formula (II), $R_3$ represents a primary alkyl group having 1 to 36 carbon atoms or an aryl group having 6 to 36 carbon atoms.

22. The process as claimed in claim 1, wherein the substituent on the aryl group is selected so as to make the sum of $\sigma_p$ values 0.0 or lower.

23. The process as claimed in claim 1, wherein m is O.

* * * * *